United States Patent [19]
Arzbaecher et al.

[11] Patent Number: 5,527,344
[45] Date of Patent: Jun. 18, 1996

[54] PHARMACOLOGIC ATRIAL DEFIBRILLATOR AND METHOD

[75] Inventors: Robert C. Arzbaecher; Thomas E. Bump, both of Chicago; Charles E. Yurkonis, Mt. Prospect; David R. Bloem, Evergreen Park, all of Ill.

[73] Assignee: Illinois Institute of Technology, Chicago, Ill.

[21] Appl. No.: 283,406

[22] Filed: Aug. 1, 1994

[51] Int. Cl.$^6$ ........................................ A61N 1/39
[52] U.S. Cl. ................................................. 607/3
[58] Field of Search ................. 607/3, 4, 5; 604/20

[56] References Cited

U.S. PATENT DOCUMENTS

| | | |
|---|---|---|
| 3,923,060 | 12/1975 | Ellinwood, Jr. . |
| 4,003,379 | 1/1977 | Ellinwood, Jr. . |
| 4,291,699 | 9/1981 | Geddes et al. . |
| 4,552,561 | 11/1985 | Eckenhoff et al. . |
| 4,586,508 | 5/1986 | Batina et al. . |
| 4,774,951 | 10/1988 | Osypka . |
| 4,892,100 | 1/1990 | Schaldach . |
| 4,969,873 | 11/1990 | Steinbach et al. . |
| 5,014,698 | 5/1991 | Cohen ........................................ 607/4 |
| 5,041,107 | 8/1991 | Heil, Jr. . |
| 5,207,219 | 5/1993 | Adams et al. . |
| 5,220,917 | 6/1993 | Cammilli et al. . |
| 5,265,600 | 11/1993 | Adams et al. . |
| 5,267,559 | 12/1993 | Jin et al. . |
| 5,269,298 | 12/1993 | Adams et al. . |
| 5,279,291 | 1/1994 | Adams et al. . |
| 5,282,836 | 2/1994 | Kreyenhagen et al. . |
| 5,282,837 | 2/1994 | Adams et al. . |
| 5,304,139 | 4/1994 | Adams et al. . |

OTHER PUBLICATIONS

Arzbaecher, R., et al., "Implantable Pharmacologic Atrial Defibrillator", *European Journal of Cardiac Pacing and Electrophysiology (Cardiostim)*, vol. 4, No. 2, Jun. 1994.

Arzbaecher, R., et al., "Computerized Control of Drug Infusion for Arrhythmia Management", *RBM*, vol. 7, No. 2, pp. 90–94, 1985.

Bump, Thomas E., et al., "Optimal Control of Antiarrhythmic Drug Infusion", *Infusion Systems in Medicine*, Eds: WD Ensminger, JL Selam, Mount Kisco, NY, Futura Publishing Co., Inc., pp. 249–261, 1987.

Bump, Thomas E., et al., "Automatic Implantable Drug Delivery for Conversion of Experimental Atrial Fibrillation", *Update in Drug Delivery Systems*, Eds: WD Ensminger, JL Selman, Mount Kisco, NY, Futura Publishing Co., Inc., pp. 303–309, 1989.

Arzbaecher, Robert, et al., "Development of an Automatic Implanted Drug Infusion System for the Management of Cardiac Arrhythmias", *Proceedings of the IEEE*, vol. 76, No. 9, pp. 1204–1209, Sep. 1988.

Arzbaecher, Robert., et al., "Use of a DDD Pacemaker to Control an Implantable Antiarrhythmic Drug Pump: System Configuration", *RBM*, vol. 12, No. 3, p. 191, 1990. Abstract.

*Primary Examiner*—William E. Kamm
*Assistant Examiner*—Scott M. Getzow
*Attorney, Agent, or Firm*—Speckman, Pauley & Fejer

[57] ABSTRACT

A method and an implantable apparatus for automatically delivering a defibrillating drug to a patient upon detection of the onset of atrial fibrillation. Atrial activity of a heart is detected and monitored. A delivery time is continuously computed and a delivery signal is emitted as a function of the monitored level of the atrial activity. When the delivery signal is emitted, an infusion pump discharges a defibrillating drug into the bloodstream of the patient. The atrial activity is also continuously monitored for computing a pacing time at which a pacing signal is emitted as a second function of the monitored level of atrial activity. When the pacing signal is emitted a pacer paces the atrium of the heart.

19 Claims, 4 Drawing Sheets

PHARMACOLOGIC ATRIAL DEFIBRILLATOR AND METHOD

The U.S. Government has a paid-up license in this invention and the right in limited circumstances to require the patent owner to license others on reasonable terms as provided for by the terms of Grant Number 5-R01-HL32131 awarded by the National Institutes of Health.

BACKGROUND OF THE INVENTION

1. Field of the Invention is invention relates to an atrial defibrillator apparatus and a method for automatic intravenous delivery of a defibrillating drug into the bloodstream of a patient in need of atrial defibrillation.

2. Description of Related Art

Atrial fibrillation (AF) is the cardiac arrhythmia that seems to occur most frequently. Although it is not usually life threatening, cardiac arrhythmia is associated with strokes apparently caused by blood clots that form after prolonged AF. The onset of AF is often unexpected and occurs suddenly. Drugs are currently available for atrial defibrillation by intravenous infusion. However, intravenous delivery often requires specialized skills of medical personnel at relatively remote facilities. AF can also be treated with a discharge of electrical energy to the heart, through the skin of the patient, by way of an external defibrillator of the type well known to those skilled in the art. This treatment is commonly referred to as synchronized cardioversion and, as its name implies, involves applying electrical defibrillating energy to the chest in synchronism with a detected ventricular electrical activation (R wave) of the heart. Such treatment is very painful and requires skills and special facilities found only in treatment centers such as hospitals.

Certain disadvantages associated with conventional implantable electrical atrial defibrillators have prevented mass production and common use as means for treating AF. U.S. Pat. No. 5,265,600 teaches a device that delivers defibrillating electrical energy to the atria via intracardiac electrodes. As with many other conventional defibrillators, such energy often results in the patient experiencing severe pain. Such energy may also induce ventricular fibrillation, which can be a fatal cardiac arrhythmia.

It is known that after successful defibrillation of the atria, the atria of the heart typically beat at a low rate, particularly if there is temporary sinoatrial node dysfunction resulting from the defibrillation of the atria. The sudden reduction in cardiac rate could potentially result in the patient experiencing a spell of dizziness. In addition, the sudden reduction in cardiac rate can also lead to dispersion of refractoriness which, if it occurs together with an R on T condition, can render the heart more vulnerable to ventricular fibrillation. Hence, such a sudden reduction in cardiac rate following successful defibrillation of the atria may be quite undesirable.

The implantable atrial defibrillation apparatus and method of this invention overcomes the disadvantages associated with conventional electrical atrial defibrillation apparatuses by using pharmacologic atrial defibrillation instead. This invention also overcomes the problem of low heart rates normally encountered after defibrillation, by automatically pacing the atrium, if required. Another advantage of this invention is that it automatically provides this same type of pacing, known in the art as the AAI mode, under circumstances such as sinus node dysfunction, and thus can aid in preventing atrial fibrillation in some patients.

SUMMARY OF THE INVENTION

It is thus one object of the present invention to provide an implantable pharmacologic atrial defibrillator for automatic delivery of an intravenous infusion of a defibrillation drug at a calculated time, to a patient in need of atrial defibrillation.

It is another object of this invention to provide a method for automatic intravenous delivery of a defibrillating drug to a patient in need of atrial defibrillation, as well as continuous monitoring of atrial activity for pacing the atrium whenever necessary.

The above and other objects of this invention are accomplished with a fully automatic, implantable pharmacologic atrial defibrillator which, in view of conventional electrical defibrillators, reduces the potential risk of induced ventricular fibrillation which may result from the delivery of defibrillating electrical energy to the atria and also eliminates the pain associated with electrical atrial defibrillation. More specifically, the pharmacologic atrial defibrillator apparatus according to this invention also continuously monitors and when necessary paces the atria to maintain adequate heart rate, particularly after pharmacologic defibrillation, but even at any other time that such pacing is needed.

The atrial defibrillator according to this invention detects atrial activity (AA) of the heart and uses such information to determine when the atria of the heart are in need of defibrillation. The atrial defibrillator of this invention intravenously delivers a defibrillating drug into the bloodstream of a patient automatically upon detection of atrial fibrillation, and also paces the atria of the heart, if required, after atrial defibrillation or at any other time.

One preferred embodiment of the method according to this invention includes the step of detecting atrial activity of the heart and determining when the atria of the heart are in need of defibrillation. A defibrillating drug is automatically delivered according to an optimal infusion rule when the patient is in need of atrial defibrillation. The method according to this invention also includes pacing the atria of the heart, if required, after automatically delivering the defibrillating drug, as well as monitoring and pacing the atria of the heart, if required, at any other time.

BRIEF DESCRIPTION OF THE DRAWINGS

The present invention, together with further objects and advantages thereof, may best be understood by reference to the following description taken in conjunction with the accompanying drawing, wherein.

DETAILED DESCRIPTION OF PREFERRED EMBODIMENTS

Figure 1:
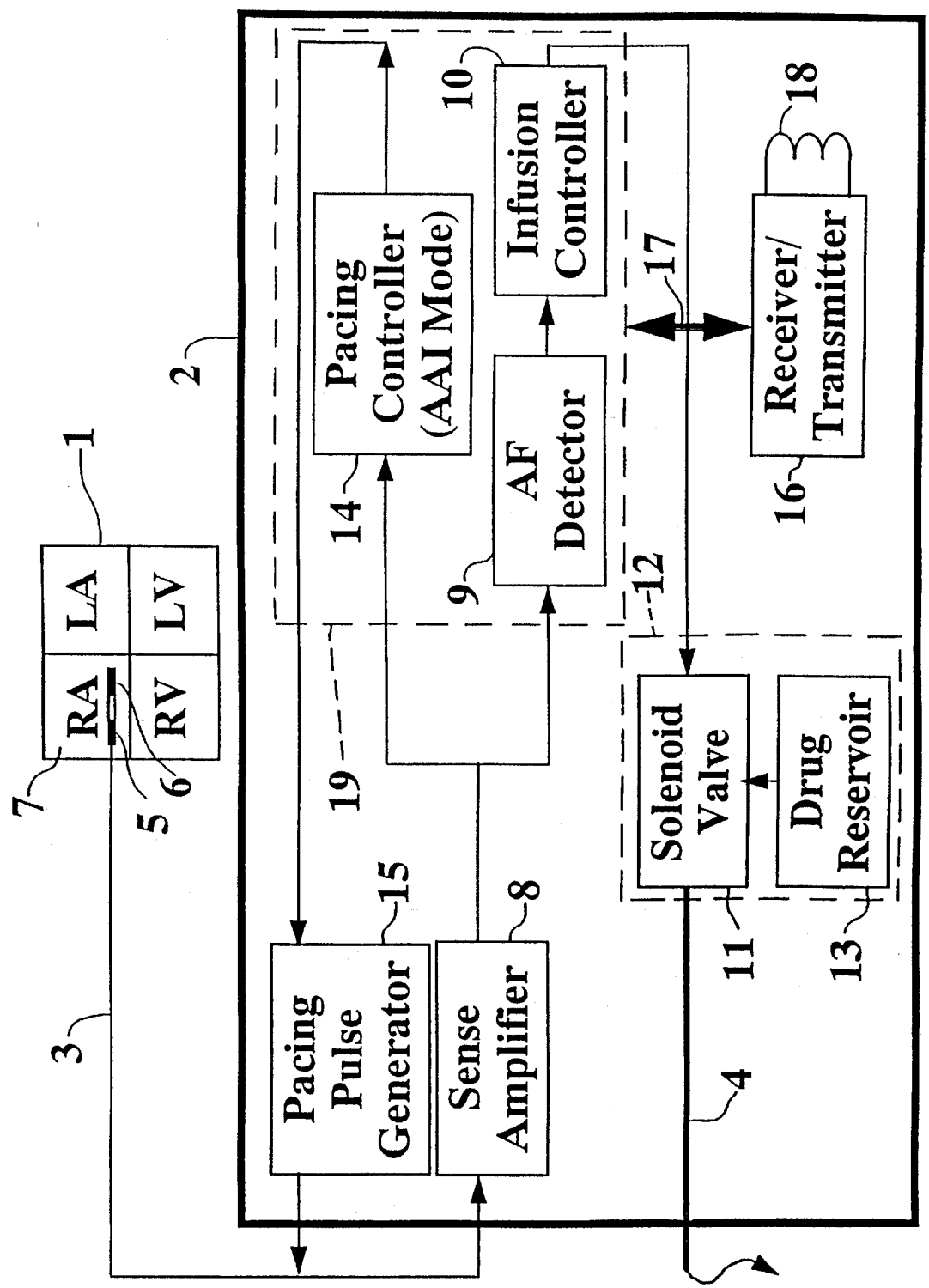
FIG. 1 is a schematic block diagram of a fully implantable pharmacologic atrial defibrillator, according to one preferred embodiment of this invention.

A pharmacologic atrial defibrillator, according to one preferred embodiment of this invention, generally comprises one or more enclosures 2, as schematically shown in FIG. 1, for hermetically sealing internal circuit elements and drug storing and dispensing elements associated with the atrial defibrillator, an endocardial lead 3 and an intravenous catheter 4. The enclosure 2, the lead 3 and the catheter 4 are designed and physically arranged to be implanted beneath the skin of a patient so as to render the apparatus of the pharmacologic atrial defibrillator fully implantable.

The endocardial lead 3 preferably comprises an endocardial bipolar lead having electrodes 5 and 6 arranged for establishing electrical contact preferably with the interior of the right atrium. For example, the lead 3 can be introduced into an appropriate vein and fed through the inferior or superior vena cava into the right atrium. The catheter 4 has a central lumen for carrying drug and when the apparatus is implanted, a discharge end of the catheter 4 is in fluid communication with an appropriate vein and thus the bloodstream of the patient. The art of implantation of the enclosure 2, the lead 3 and the catheter 4 is well-known to those skilled in the art.

Within the enclosure 2, according to one preferred embodiment of this invention, the pharmacologic atrial defibrillator comprises a sense amplifier 8, an atrial fibrillation (AF) detector 9, an infusion controller 10 and a drug pump 12, as schematically shown in FIG. 1. The sense amplifier 8 forms a detecting means which, together with the lead 3 to which the sense amplifier 8 is connected, detects atrial activations of a right atrium 7 of a heart 1. The output of the sense amplifier 8 is preferably coupled to a microprocessor-based AF detector 9 which identifies the onset of AF, particularly by one preferred method of signal processing to be described hereinafter. When AF is detected, a microprocessor-based infusion controller 10 causes, by one preferred method to be described hereinafter, a sequence of electrical pulses which are delivered to a solenoid valve 11 of the drug pump 12. The drug pump 12 preferably comprises a reservoir 13 for storing a defibrillating drug.

In one preferred embodiment, the output of the sense amplifier 8 is also coupled to a microprocessor-based AAI pacing controller 14, which controls an atrial pacing pulse generator 15 to provide AAI mode atrial pacing via the endocardial lead 3, according to a method well-established in the art.

The microprocessor-based AF detector 9 performs an estimate of atrial rate based on the median of the interval between atrial activations. This is in distinction to conventional detectors which base the estimate of heart rate on the mean or average of the interval between activations. The advantage of median estimators over mean estimators is that median estimators minimize the deleterious effect of so-called outlier intervals caused by occasional under-sensing, which is known to occur during AF.

Figure 2:
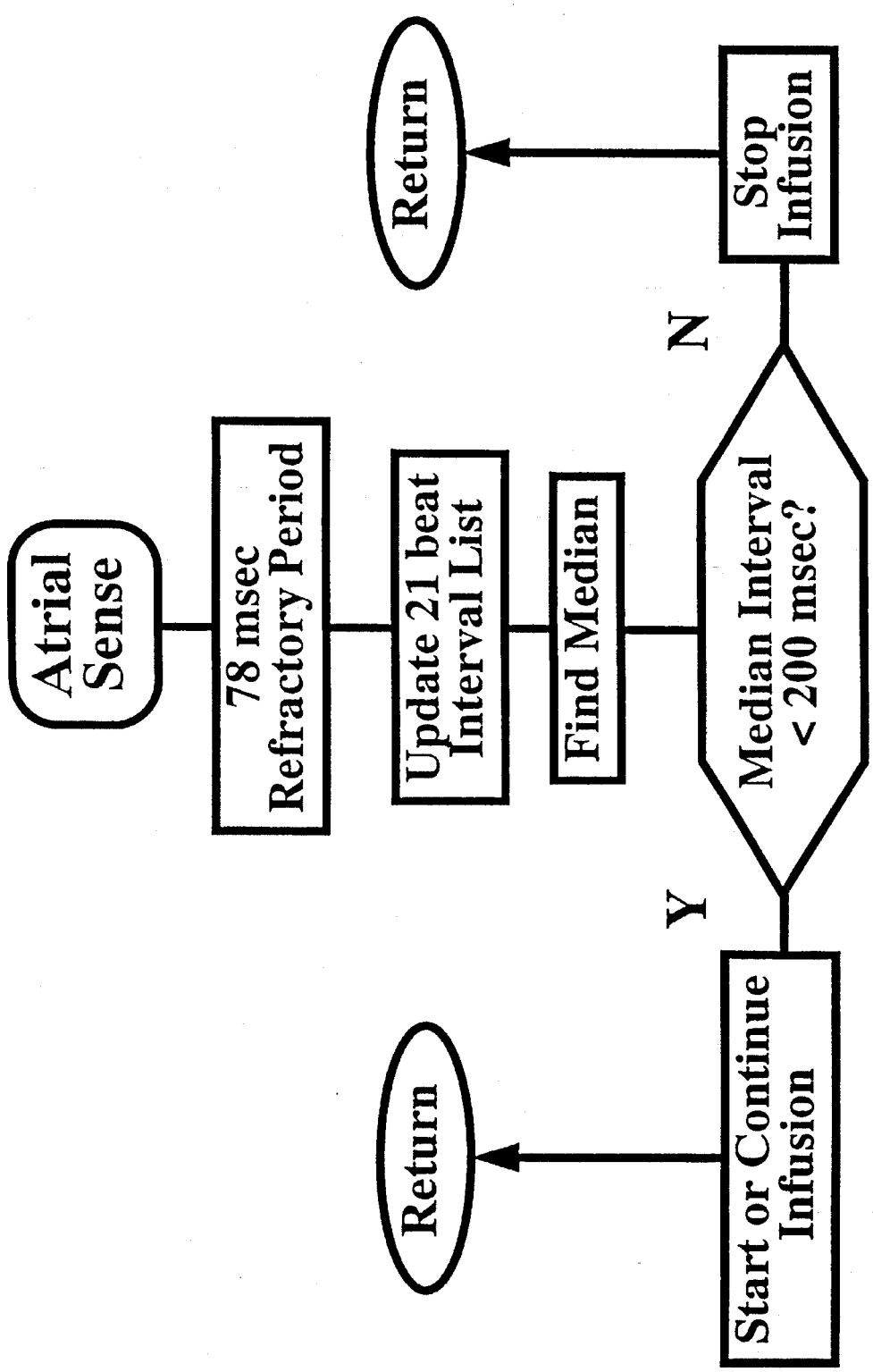
FIG. 2 is a flow diagram illustrating one preferred embodiment of an apparatus and a method for detection of atrial fibrillation, according to this invention.

One preferred embodiment of the AF detector 9 of this invention is described with respect to the flow diagram of FIG. 2. An atrial sense starts a refractory period which prevents multiple sensing of a single activation. Senses occurring during the refractory period are ignored. At the end of the refractory period, the time between a current atrial sense and a previous atrial sense is added to the list of atrial activation intervals. A sorting algorithm is then called, which is designed to minimize the number of comparisons necessary to find the median element of the interval list. The median is then compared to the interval threshold of approximately 200 milliseconds, for example. If the median estimate is greater than the interval threshold, no action is taken. If less than, AF is detected and the infusion controller is activated.

Designing a rhythm detection algorithm based on AA interval measurements requires consideration of the front-end hardware used for atrial sensing and the behavior of the atrial signal during both normal rhythm and AF. An atrial sense is registered when an atrial depolarization exceeds a fixed threshold after being high-pass filtered at 30 Hz, for example. This filter setting, while appropriate for SR, considerably attenuates AF, whose power spectrum contains little energy above 30 Hz. Additionally, AF demonstrates a considerable drop in signal amplitude as compared to SR even without filtering. The combination of these factors has been observed to cause frequent undersensing of AF resulting in an inadequate number of beats to diagnose AF and thus failure to begin infusion. To improve sensing of AF, median filtering of derived AA intervals as an alternative to simple beat counting can be used.

Undersensing during AF produces artificially long detected AA intervals, which become "outliers" in the record of recent AA intervals used to estimate rate. The robustness of a rate estimator to the presence of outliers is determined by its breakpoint, which is the smallest number of outliers needed to degrade the estimate. The median possesses the best possible breakpoint since at least half the intervals must be outliers in order to corrupt the median. Hence, if at least N/2 of the last N observed AA intervals are less than the detection threshold, AF will be diagnosed.

According to one preferred embodiment of this invention, rhythm discrimination via median filtering is accomplished via a bubble-sort ranking of the AA interval record in an N element array SINT such that $SINT[I] \leq SINT[I+1]$, $I \in \{1, N\}$. An interval estimate is made using the median element of SINT, namely $SINT[(N+1)/2]$. AF is diagnosed and infusion started if the interval estimate is less than an arbitrary threshold of 200 msec, for example. Infusion is terminated by either an interval estimate greater than a specified time period, such as 330 msec (<180 bpm), or failure to convert within a given time period, such as 30 minutes.

Figure 3:
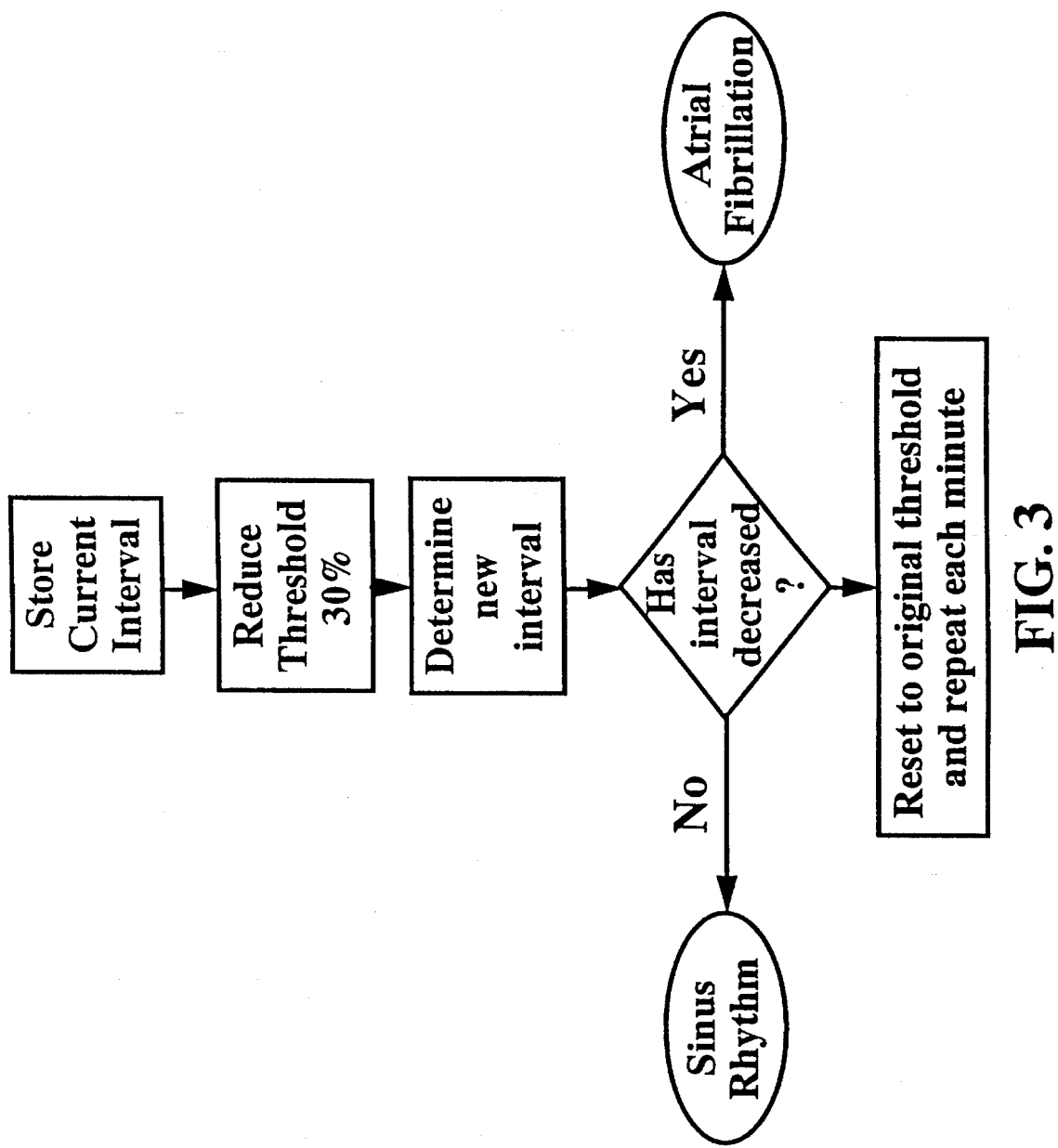
FIG. 3 is a flow diagram illustrating another preferred embodiment according to this invention wherein threshold-scanning is used to detect atrial fibrillation.

An alternative preferred embodiment of a microprocessor-based AF detector 9, according to this invention, uses a threshold-scanning method. When a sensing threshold is lowered in a pacemaker sense amplifier, the interval between activations sensed during AF decreases, while that during normal sinus rhythm does not. This is because the amplitude of individual activations in the electrogram during AF is known to be quite variable, while the amplitude of individual activations during normal sinus rhythm is known to be relatively constant. Thus, in AF, reducing the sensing threshold reduces the interval between successive atrial sensings, while no such action occurs during sinus rhythm. The threshold scanning method according to one preferred embodiment of this invention can be described with respect to FIG. 3. Each minute, or other suitable time interval, the microprocessor temporarily stores the current estimate of interval between atrial activation sensings whether based on a median estimate as described above or on a conventional estimate. The microprocessor then reduces the sensing threshold in the sense amplifier 8 by, for example, approximately 30% and re-estimates the interval between atrial activation sensings to determine a new interval. The new interval is then compared to the original interval. If the new interval is less than the original interval by a significant or predetermined amount, AF is present and the infusion controller 10 is activated. If the new interval is not less than the original interval by the significant or predetermined amount, the infusion controller 10 is not activated.

The threshold scanning method for AF detection can also be implemented with a digitized representation of the amplified atrial electrogram, as would be available in a microprocessor equipped with an A/D converter. This would permit threshold scanning of the identical period of atrial activation, thus eliminating any effect on interval caused, for example, by a change in patient posture or activity which may occur during successive threshold scans.

The microprocessor-based controller 10 causes the defibrillating drug to be infused intravenously in such a way as to produce therapeutic blood levels of the drug very rapidly and maintain these levels until atrial defibrillation occurs. Most antiarrhythmic drugs follow a two-compartment pharmacokinetic model. It is known that in this model the infusion method for realizing rapid rise and subsequent maintenance of therapeutic levels includes an initial rapid rate of delivery followed by a rate which decreases exponentially to a standard maintenance rate sufficient to offset drug lost by elimination. In one preferred embodiment of this invention, this infusion method is implemented by a model-based algorithm which periodically computes the concentration of the drug in the blood, such as according to the well-known mathematical laws of two-compartment pharmacokinetics. When the computed concentration is below the desired concentration a known amount of drug is delivered. When the computed concentration is at or above the desired concentration level no drug is delivered.

More specifically, an optimal infusion protocol preferably produces therapeutic plasma levels in a timely fashion without overshooting the desired level. For drugs with two compartment pharmacokinetic behavior, including most anti-arrhythmics, it is known that an "exponentially-tapering" infusion matched to the known distribution dynamics of the drug is optimal. The two compartment equations are given by:

$$\dot{C}_1 = r(t)/V_1 - k_{10}C_1 - k_{12}(C_1 - C_2) \qquad \text{Equation 1}$$

$$\dot{C}_2 = k_{21}(C_1 - C_2) \qquad \text{Equation 2}$$

where $C_1$ and $C_2$ are the central and peripheral compartment concentrations, r(t) is the rate of infusion into the central compartment, $V_1$ is the central compartment volume, and $k_{10}$, $k_{12}$, and $k_{21}$ are the time constants for elimination from the central compartment, transfer from the central compartment to the periphery, and transfer from the periphery to the central compartment, respectively. The desired concentration $C_{1d}$ can be initially achieved with a loading bolus equal to $C_{1d} V1$. Maintaining this concentration involves solving for r(t) with the constraint that $C_1 = C_{1d}$. This solution for r(t) is given as:

$$r(t) = V_1 k_{10} C_{1d} + V_1 k_{12} C_{1d} e^{-k_{21}t} \qquad \text{Equation 3}$$

which includes a constant maintenance drip plus an exponentially decreasing component.

One implementation drawback of the exponentially-tapering infusion is that Equation 3 requires a variable-speed pump capable of continuous flow rate adjustment. However, on-off control of a constant speed pump 12 via pulse-frequency modulation, according to this invention, provides an excellent approximation to the exponentially-tapering infusion. The on-off control scheme can be easily derived by substituting the derivative operators in Equations 1 and 2 with finite difference operators and replacing the continuous rate term involving r(t) with a switching function which allows for discrete concentration increases. The resulting equations are:

$$C_1[n] = C_1[n-1][1-(k_{10}+k_{12})T] + k_{12}TC_2[n-1] + S(C_{pulse}) \qquad \text{Equation 4}$$

$$C_2[n] = C_2[n-1][1-k_{21}T] + k_{21}TC_1[n-1] \qquad \text{Equation 5}$$

where n is the discrete time index, T is the discrete time increment, and S(Cpulse) is a switching function controlling concentration increase due to each valve opening. In one preferred embodiment of this invention, for example, the drug delivered with each valve opening is 2.65 mg. The resulting increase in concentration is then given by:

$$S(C_{pulse}) = 2.65/V_1 \ mg/L \text{ for } C_1[n-1] \leq C_{1d} \qquad \text{Equation 6}$$

$$S(C_{pulse}) = 0 \text{ otherwise.} \qquad \text{Equation 6}$$

Figure 4:
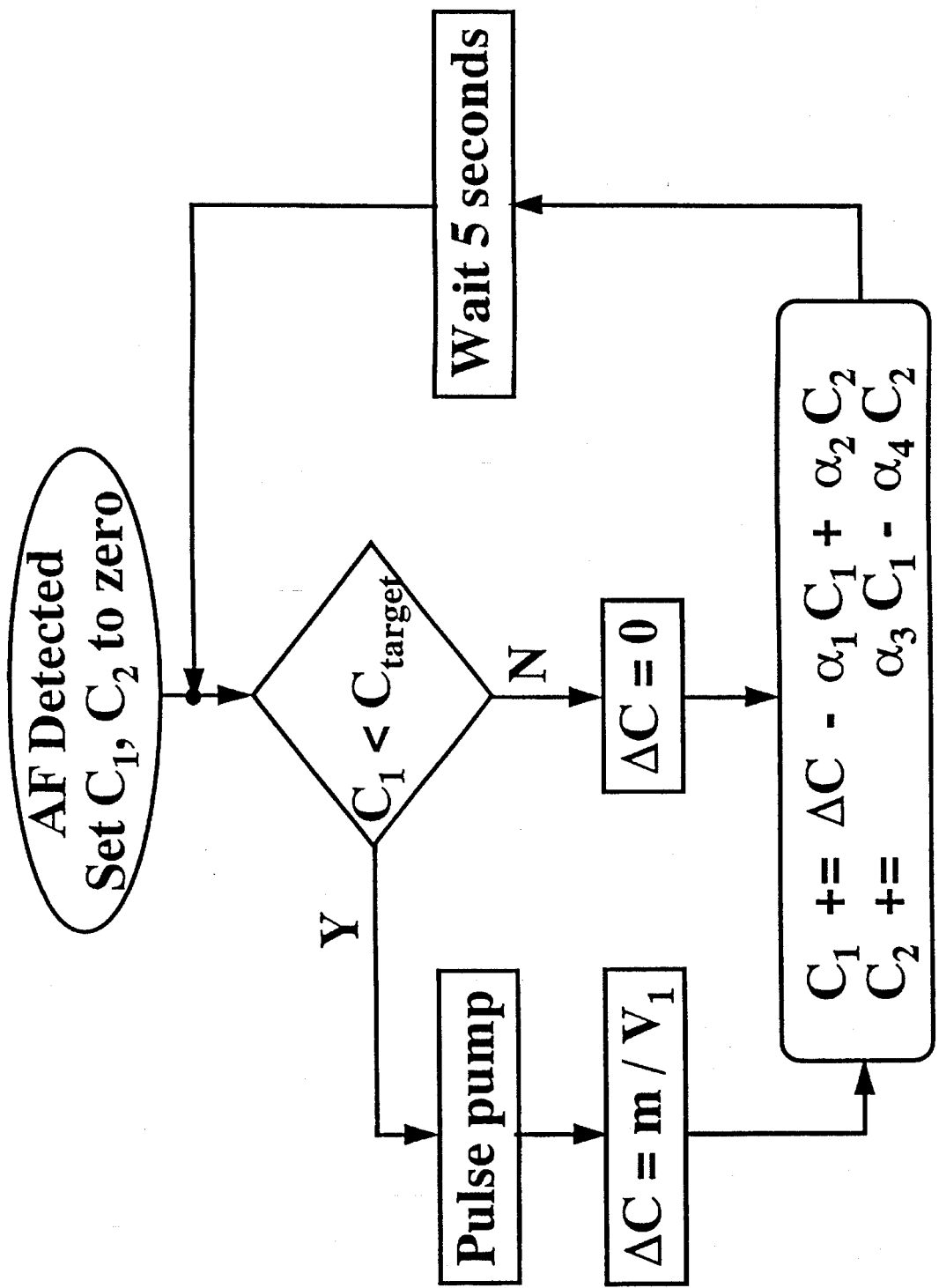
FIG. 4 is a flow diagram illustrating a method of infusion control, according to still another preferred embodiment of this invention.

One preferred embodiment of a detailed method of the infusion controller 10 can be described with respect to FIG. 4. Once AF has been detected, the blood concentration C1 and peripheral compartment concentration C2 are initialized. A comparison is then made to determine if the blood concentration as calculated from two-compartment pharmacokinetic equations is less than the target level. If so, the solenoid valve 11 is pulsed, the concentration increase from pumping the drug is computed and the new compartmental concentrations are calculated by an Euler approximation to the two-compartment differential equations. The system waits during a predetermined time period, approximately 5 seconds for example, and repeats until C1 reaches the target concentration. Then the infusion pump 12 is not activated The model-based, "pulsatile" nature of this infusion avoids the need for exponential calculations and need for a variable speed pump.

The infusion pump 12 which includes the solenoid valve 11 and the drug reservoir 13, as well as a refilling port, are well-known to those skilled in the art. An example of a suitable infusion pump is described by U.S. Pat. No. 5,220,917.

For entering operating parameters into a microprocessor 19, the microprocessor 19 receives such programmable operating parameters from an external controller which is preferably external to the skin of the patient. The external controller is arranged to communicate with a receiver/transmitter 16 which is coupled to the microprocessor 19 over a bi-directional bus 17. The receiver/transmitter 16 may be of the type well known to those skilled in the art for conveying various information which the receiver/transmitter 16 obtains from the microprocessor 19 to the external controller or for receiving programming parameters from the external controller which the receiver/transmitter 16 then conveys to the microprocessor 19 for storage in internal memory.

The receiver/transmitter 16 preferably includes a transmitting coil 18 so that the receiver/transmitter 16 and the transmitting coil 18 form a communication means. Such communication means are well known to those skilled in the art and may be utilized as noted above for receiving commands from the external controller to the implantable enclosure 2 and for transmitting data to the external controller from the implanted enclosure 2. One such communication system is disclosed, for example, by U.S. Pat. No. 4,586,508.

To complete the identification of the various structural elements within the enclosure 2, the atrial defibrillator according to this invention further comprises a depletable power source, such as a lithium battery, which supplies power to the electrical components of the atrial pharmacologic defibrillator.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

What is claimed is:

1. A method for delivering upon demand a defibrillating drug to a patient, the method comprising the steps of:
    (a) detecting and monitoring a level of atrial activity and a level of ventricular activity of a heart of the patient;
    (b) continuously computing a delivery time to emit a delivery signal as a first function of the monitored level of atrial activity;
    (c) emitting the delivery signal at the computed delivery time to delivery means for introducing the defibrillating drug into a bloodstream of the patient;
    (d) continuously computing a pacing time to emit a pacing signal as a second function of the monitored level of atrial activity and ventricular activity; and
    (e) emitting the pacing signal at the computed pacing time to pacing means for pacing an atria of the heart.

2. A method for delivering upon demand a defibrillating drug to a patient, the method comprising the steps of:
    (a) detecting and monitoring a level of atrial activity of a heart of the patient by estimating an atrial rate using a median value of an interval between atrial activations;
    (b) continuously computing a delivery time to emit a delivery signal as a first function of the monitored level of atrial activity;
    (c) emitting the delivery signal at the computed delivery time to delivery means for introducing the defibrillating drug into a bloodstream of the patient;
    (d) continuously computing pacing time to emit a pacing signal as a second function of the monitored level of atrial activity; and
    (e) emitting the pacing signal at the computed pacing time to pacing means for pacing an atria of the heart.

3. A method for delivering upon demand a defibrillating drug to a patient, the method comprising the steps of:
    (a) detecting and monitoring a level of atrial activity of a heart of the patient;
    (b) continuously computing a delivery time to emit a delivery signal by computing a median value of a plurality of sensed time intervals each occurring between two atrial senses, comparing the median value to a threshold value, and emitting the delivery signal when the median value is less than a threshold value;
    (c) emitting the delivery signal at the computed delivery time to delivery means for introducing the defibrillating drug into a bloodstream of the patient;
    (d) continuously computing pacing time to emit a pacing signal as a second function of the monitored level of atrial activity; and
    (e) emitting the pacing signal at the computed pacing time to pacing means for pacing an atria of the heart.

4. A method according to claim 3 wherein the threshold value is approximately 200 milliseconds.

5. A method for delivering upon demand a defibrillating drug to a patient, the method comprising the steps of:

(a) detecting and monitoring a level of atrial activity of a heart of the patient;
    (b) continuously computing a delivery time to emit a delivery signal by establishing a first threshold value of an interval between successive atrial sensings, reducing the first threshold value and establishing a second threshold value, comparing a first interval corresponding to the first threshold value to a second interval established by the second threshold value, and emitting the delivery signal upon detection of the second interval being less than the first interval by a predetermined amount;
    (c) emitting the delivery signal at the computed delivery time to delivery means for introducing the defibrillating drug into a bloodstream of the patient;
    (d) continuously computing a pacing time to emit a pacing signal as a second function of the monitored level of atrial activity; and
    (e) emitting the pacing signal at the computed pacing time to pacing means for pacing an atria of the heart.

6. A method for delivering upon demand a defibrillating drug to a patient, the method comprising the steps of:
    (a) detecting and monitoring a level of atrial activity of a heart of the patient;
    (b) continuously computing a delivery time to emit a delivery signal by calculating a concentration of the defibrillating drug in the bloodstream, and pulsing the delivery means to introduce the defibrillating drug into the bloodstream when the concentration is below a predetermined value;
    (c) emitting the delivering signal at the computed delivery time to delivery means for introducing the defibrillating drug into the bloodstream of the patient;
    (d) continuously computing a pacing time to emit a pacing signal as a second function of the monitored level of atrial activity; and
    (e) emitting the pacing signal at the computed pacing time to pacing means for pacing an atria of the heart.

7. A method according to claim 6 wherein the concentration is calculated with a two-compartment pharmacokinetics equation using a blood concentration value C1 and a peripheral compartment concentration value C2.

8. A method according to claim 6 wherein the delivery means introduces the defibrillating drug into the bloodstream in pulsed amounts.

9. An implantable apparatus for automatically delivering upon demand a defibrillating drug to a patient, the apparatus comprising:
    sensor means for sensing and monitoring a level of atrial activity of a heart of a patient;
    first computer means for computing a delivery time and emitting a delivery signal as a function of said monitored level of atrial activity;
    delivery means for introducing the defibrillating drug into a bloodstream of the patient at said delivery time;
    second computer means for continuously computing a pacing time and emitting a pacing signal as a second function of said monitored level of atrial activity;
    pace means for receiving said pacing signal and pacing an atria of said heart at said pacing time;
    at least one hermetically sealed enclosure; and
    said first computer means, said second computer means, said delivery means and said pacing means housed within said at least one hermetically sealed enclosure.

10. An apparatus according to claim 9 wherein said sensor means comprise a lead having one end adapted for contacting an endocardium of said heart and an opposite end in communication with at least one of said first computer means and said second computer means.

11. An apparatus according to claim 10 wherein said lead is an endocardial lead, said one end of said endocardial lead comprising two electrodes each adapted for contacting an interior surface of a right atrium of said heart.

12. An apparatus according to claim 10 wherein said first computer means comprise an amplification means for amplifying an atrial signal communicated through said lead.

13. An apparatus according to claim 9 wherein said first computer means comprise atrial defibrillation means for detecting an onset of atrial fibrillation as a function of a sensed and amplified signal received from said sensor means.

14. An apparatus according to claim 13 wherein said first computer means comprise an infusion controller in communication with said atrial defibrillation means, and said infusion controller computing and emitting said delivery signal to said delivery means at said delivery time.

15. An apparatus according to claim 9 wherein said delivery means comprise an infusion pump having an inlet in fluid communication with a reservoir containing a defibrillating drug and an outlet adapted for fluid communication with said bloodstream.

16. An apparatus according to claim 15 wherein said delivery means further comprise a solenoid valve forming fluid communication between said inlet and said outlet upon receipt of said delivery signal.

17. An apparatus according to claim 9 wherein said delivery means comprise a defibrillating drug reservoir, a catheter having one end in communication with said defibrillating drug reservoir and an opposite end adapted for communication with said bloodstream.

18. An apparatus according to claim 9 wherein said second computer means comprise a pulse generator, a pacing controller emitting said pacing signal to said pulse generator as a function of a sensed and amplified signal received from said sensor means.

19. An apparatus according to claim 18 further comprising a lead having one end adapted for contacting an endocardium of said heart, and said pulse generator delivering an output voltage through said lead.

* * * * *